US009981878B2

(12) United States Patent
Feist et al.

(10) Patent No.: US 9,981,878 B2
(45) Date of Patent: May 29, 2018

(54) MULTI-FUNCTIONING MATERIAL COMPOSITIONS, STRUCTURES INCORPORATING THE SAME AND METHODS FOR DETECTING AGEING IN LUMINESCENT MATERIAL COMPOSITIONS

(75) Inventors: Jörg Peter Feist, London (GB); John Rayment Nicholls, Buckinghamshire (GB)

(73) Assignee: Sensor Coating Systems Limited, Surrey (GB)

( * ) Notice: Subject to any disclaimer, the term of this patent is extended or adjusted under 35 U.S.C. 154(b) by 1664 days.

(21) Appl. No.: 12/994,379

(22) PCT Filed: May 26, 2009

(86) PCT No.: PCT/GB2009/001305
§ 371 (c)(1),
(2), (4) Date: Jul. 18, 2011

(87) PCT Pub. No.: WO2009/141632
PCT Pub. Date: Nov. 26, 2009

(65) Prior Publication Data
US 2011/0266459 A1    Nov. 3, 2011

(30) Foreign Application Priority Data

May 23, 2008 (GB) .................................. 0809440.1

(51) Int. Cl.
*G01N 21/64* (2006.01)
*C04B 35/486* (2006.01)
(Continued)

(52) U.S. Cl.
CPC .......... *C04B 35/486* (2013.01); *C01G 25/006* (2013.01); *C01G 25/02* (2013.01);
(Continued)

(58) Field of Classification Search
USPC ............................................ 250/458.1, 459.1
See application file for complete search history.

(56) References Cited

U.S. PATENT DOCUMENTS 5,281,825 A * 1/1994 Berndt et al. .............. 250/458.1
5,656,564 A 8/1997 Nakayama
(Continued)

FOREIGN PATENT DOCUMENTS

EP    0 354 573    2/1990
JP    07 215758    8/1995
(Continued)

OTHER PUBLICATIONS

International Search Report for corresponding application No. PCT/GB2009/001305 dated Sep. 2, 2009.

*Primary Examiner* — Christine S Kim
(74) *Attorney, Agent, or Firm* — Renner, Otto, Boisselle & Sklar, LLP

(57) ABSTRACT

A multi-functional material composition comprising a zirconia host and containing a luminescent lanthanide oxide additive, in particular dysprosia ($Dy_2O_3$), wherein the lanthanide oxide additive is effective both in stabilizing the zirconia and providing for luminescent temperature sensing, and a method of determining a remaining useful life-time for the luminescent material composition from the proportion of a monoclinic phase (m) in the material composition.

26 Claims, 9 Drawing Sheets

Figure 1:
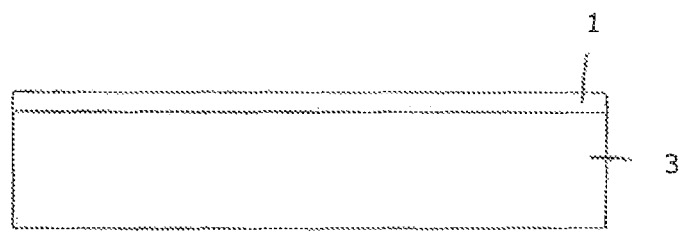

(51) Int. Cl.
*C01G 25/00* (2006.01)
*C01G 25/02* (2006.01)
*C09K 11/77* (2006.01)
*C23C 28/04* (2006.01)
*G01N 21/84* (2006.01)

(52) U.S. Cl.
CPC ........ *C09K 11/7769* (2013.01); *C23C 28/042* (2013.01); *G01N 21/643* (2013.01); *G01N 21/6408* (2013.01); *C01P 2002/52* (2013.01); *C04B 2235/3224* (2013.01); *C04B 2235/3225* (2013.01); *C04B 2235/76* (2013.01); *C04B 2235/765* (2013.01); *G01N 2021/8427* (2013.01)

(56) References Cited

U.S. PATENT DOCUMENTS

| | | | |
|---|---|---|---|
| 7,690,840 B2* | 4/2010 | Zombo et al. | 374/121 |
| 8,173,266 B2* | 5/2012 | Choy et al. | 428/469 |
| 2003/0115941 A1* | 6/2003 | Srivastava et al. | 73/118.1 |
| 2003/0118440 A1* | 6/2003 | Zhao et al. | 415/118 |
| 2011/0003119 A1* | 1/2011 | Doesburg et al. | 428/155 |
| 2012/0264588 A1* | 10/2012 | Kolb et al. | 501/134 |

FOREIGN PATENT DOCUMENTS

| | | |
|---|---|---|
| JP | 07 215759 | 8/1995 |
| JP | 08 033701 | 2/1996 |
| WO | 2007/023292 | 3/2007 |
| WO | 2009/083729 | 7/2009 |

* cited by examiner

MULTI-FUNCTIONING MATERIAL COMPOSITIONS, STRUCTURES INCORPORATING THE SAME AND METHODS FOR DETECTING AGEING IN LUMINESCENT MATERIAL COMPOSITIONS

The present invention relates to multi-functional material compositions, in particular for use in high-temperature environments, structures which incorporate the same, such as coatings, for example, environmental barrier coatings (EBCs) and thermal barrier coatings (TBCs), and bulk components, for example, heat shields, and methods for detecting ageing in luminescent material compositions.

EBCs are usually multi-phase or multi-layered ceramic systems which, as at least one component thereof, include an oxide-based ceramic which contains oxygen-active elements, such as yttrium, hafnium, silicon or lanthanides, which segregate to grain boundaries and slow short-circuit transport along the grain boundaries.

TBCs are structural coatings which are applied to components which are subjected to high temperatures, often greater than 1000° C., and thus would be prone inter alia to oxidation and corrosion processes. Typical applications are in the aviation and power generation industries, particularly in the coating of turbine components, such as turbine blades, vanes or combustion liners.

As disclosed in the applicant's earlier WO-A-2000/006796, U.S. Pat. No. 6,974,641 and U.S. Pat. No. 7,510,776, the provision of luminescent materials in TBCs enables the in situ optical measurement of characteristics of the TBCs, in particular the temperature and phase change of the TBCs.

Further, as disclosed in the applicant's earlier WO-A-2005/019601, the provision of luminescent materials in TBCs enables the in-situ measurement of chemical changes within TBCs, such as hot corrosion.

U.S. Pat. No. 6,730,918 discloses the provision of luminescent materials in TBCs for determining past-service conditions and a remaining useful life-time of TBCs. This document discloses a lanthanide-doped TBC, in particular a YSZ:Eu phosphor, and the utilization of a ratio of the luminescence intensities for emission lines in determining phase concentrations and estimating the remaining useful life-time.

Existing TBCs are predominantly formed from yttria-stabilized zirconia (YSZ), though other ceramic materials, such as pyrochiores or yttrium aluminium garnets (YAG), are now being considered.

YSZ is deposited as a metastable tetragonal phase (t'), but disadvantageously, when exposed to a thermal environment, the t' phase separates into a mixture of tetragonal (t) and cubic (c) phases, and subsequently upon cooling, the t phase transforms into a monoclinic phase (m). This t→m phase transformation is disadvantageous, insofar as the transformation is associated with a volume increase, which results in cracking of YSZ TBCs and eventually causes spallation.

The formation of the m phase is directly linked with the length of time that YSZ TBCs are exposed to high temperatures, and the present inventors have developed improved methods for monitoring the proportion of the m phase in YSZ TBCs, which allow for a determination of past service conditions and the remaining useful life-time.

In one aspect the present invention provides a multi-functional material composition comprising yttria ($Y_2O_3$) partially-stabilized zirconia containing a luminescent lanthanide oxide additive, wherein the lanthanide oxide additive is effective both in stabilizing the zirconia and providing for luminescent temperature sensing.

In one embodiment the lanthanide oxide additive is a tri-valent lanthanide oxide.

Preferably, the lanthanide oxide additive is dysprosia ($Dy_2O_3$).

Preferably, the lanthanide oxide additive is included in an amount of between about 0.003 and about 4 mol %.

More preferably, the lanthanide oxide additive is included in an amount of between about 0.01 and about 4 mol %.

In one embodiment the lanthanide oxide additive is included in an amount of between about 0.3 and about 2 mol %.

In one embodiment the material composition is such that an intensity ratio for a pair of luminescent emission lines for the material composition decreases exponentially as a function of the proportion of the monoclinic (m) phase in the material composition.

In one embodiment the exponential function is fitted by the equation $R = a \cdot \exp(-\% \, m/b) + c$, where a, b and c are pre-calibrated constants, R is the intensity ratio and % m is the percentage of the m phase.

In one embodiment the exponential function is substantially independent of the amount of the lanthanide oxide additive.

In one embodiment the emission lines are at wavelengths of about 485 nm and about 493 nm.

In another embodiment the emission lines are at wavelengths of about 580 nm and about 585 nm.

In another aspect the present invention provides a multi-functional material composition comprising a zirconia host and containing a luminescent lanthanide oxide additive, wherein the lanthanide oxide additive is effective both in stabilizing the zirconia and providing for luminescent temperature sensing.

In one embodiment the lanthanide oxide additive is a tri-valent lanthanide oxide.

Preferably, the lanthanide oxide additive is dysprosia ($Dy_2O_3$).

Preferably, the lanthanide oxide additive is included in an amount of between about 0.003 and about 4 mol %.

More preferably, the lanthanide oxide additive is included in an amount of between about 0.01 and about 4 mol %.

In one embodiment the lanthanide oxide additive is included in an amount of between about 0.3 and about 2 mol %.

In one embodiment the material composition is such that an intensity ratio for a pair of luminescent emission lines for the material composition decreases exponentially as a function of the proportion of the monoclinic (m) phase in the material composition.

In one embodiment the exponential function is fitted by the equation $R = a \cdot \exp(-\% \, m/b) + c$, where a, b and c are pre-calibrated constants, R is the intensity ratio and % m is the percentage of the m phase.

In one embodiment the exponential function is substantially independent of the amount of the lanthanide oxide additive.

In one embodiment the emission lines are at wavelengths of about 485 nm and about 493 nm.

In another embodiment the emission lines are at wavelengths of about 580 nm and about 585 nm.

In a further aspect the present invention provides a method of determining the proportion of a monoclinic phase (m) in a luminescent material composition, preferably comprising a zirconia host and containing a luminescent lanthanide oxide additive, the method comprising the steps of:

determining an intensity ratio for a pair of luminescent emission lines for the material composition which decreases exponentially as a function of the proportion of the m phase in the material composition; fitting the intensity ratio to an exponential function for the material composition; and determining the proportion of the m phase in the material composition.

In one embodiment the lanthanide oxide additive is a tri-valent lanthanide oxide.

Preferably, the lanthanide oxide additive is dysprosia ($Dy_2O_3$).

Preferably, the lanthanide oxide additive is included in an amount of between about 0.003 and about 4 mol %.

More preferably, the lanthanide oxide additive is included in an amount of between about 0.01 and about 4 mol %.

In one embodiment the lanthanide oxide additive is included in an amount of between about 0.3 and about 2 mol %.

In one embodiment the material composition further contains yttria ($Y_2O_3$) and the zirconia is partially stabilized by the yttria.

In one embodiment the exponential function is fitted by the equation $R = a \cdot \exp(-\% \, m/b) + c$, where a, b and c are pre-calibrated constants, R is the intensity ratio and % m is the percentage of the m phase.

In one embodiment the exponential function is substantially independent of the amount of the lanthanide oxide additive.

In one embodiment the emission lines are at wavelengths of about 485 nm and about 493 nm.

In another embodiment the emission lines are at wavelengths of about 580 nm and about 585 nm.

In one embodiment the method is for determining a remaining useful life-time for the material composition, and the method further comprises the step of: determining a remaining useful life-time for the material composition by reference to the proportion of the m phase in the material composition.

In a still further aspect the present invention provides a method of determining the proportion of a monoclinic phase (m) in a luminescent material composition, preferably comprising a zirconia host and containing a luminescent lanthanide oxide additive, the method comprising the steps of: determining a luminescence life-time decay at room temperature for the material composition; fitting the determined life-time decay to a life-time decay curve calibrated as a function of the proportion of the m phase for the material composition; and determining the proportion of the m phase in the material composition.

In one embodiment the lanthanide oxide additive is a tri-valent lanthanide oxide.

Preferably, the lanthanide oxide additive is dysprosia ($Dy_2O_3$).

Preferably, the lanthanide oxide additive is included in an amount of between about 0.003 and about 4 mol %.

More preferably, the lanthanide oxide additive is included in an amount of between about 0.01 and about 4 mol %.

In one embodiment the lanthanide oxide additive is included in an amount of between about 0.3 and about 2 mol %.

In one embodiment the material composition further contains yttria ($Y_2O_3$) and the zirconia is partially stabilized by the yttria.

In one embodiment the method is for determining a remaining useful life-time for the material composition, and the method further comprises the step of: determining a remaining useful life-time for the material composition by reference to the proportion of the m phase in the material composition.

In yet another aspect the present invention provides a method of determining ageing of a material, the method comprising the steps of: applying an excitation signal having a periodically-varying intensity to a material including a luminescent element; detecting the luminescence signal from the material; determining a phase relationship between the excitation and luminescence signals; and determining ageing of the material from the phase relationship between the excitation and luminescence signals.

In one embodiment the excitation signal has a sinusoidal waveform.

In one embodiment the phase relationship between the excitation and luminescence signals is referenced to a look-up table.

In one embodiment the ageing of the material relates to a structural phase change.

In one embodiment the material comprises a zirconia host containing a luminescent lanthanide oxide additive.

In one embodiment the ageing of the material relates to the proportion of a monoclinic (m) phase in the material.

In one embodiment the method is for determining a remaining useful life-time for the material, and the method further comprises the step of: determining a remaining useful life-time for the material by reference to the proportion of the m phase in the material.

In still another aspect the present invention provides a method of determining the proportion of a monoclinic phase (m) in a luminescent material composition comprising a zirconia host and containing a luminescent lanthanide oxide additive, the method comprising the steps of: determining a luminescence characteristic for the material composition which varies as a function of the proportion of the m phase in the material composition; fitting the luminescence characteristic to a predetermined function for the material composition; and determining the proportion of the m phase in the material composition.

The present invention advantageously provides a multi-functional luminescent material composition, which exhibits improved long-term phase stability and provides for improved phase detection in comparison to existing luminescent compositions.

Figure 2A:
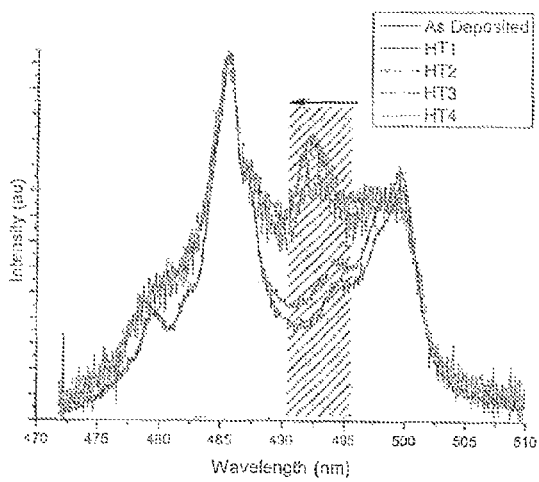
Figure 2B:
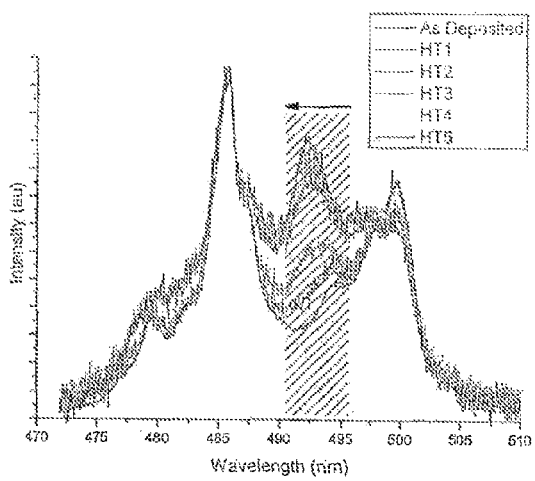
Figure 2C:
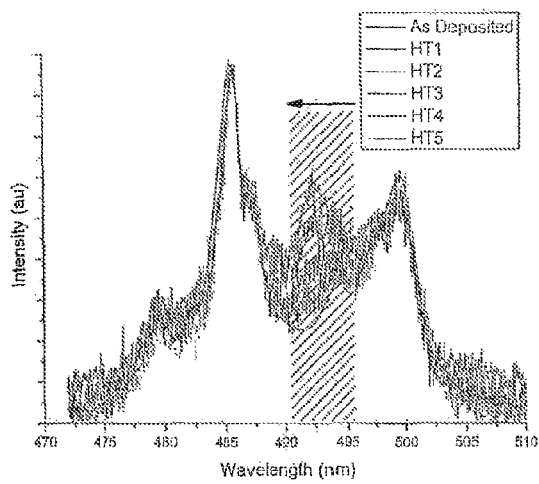
Figure 3A:
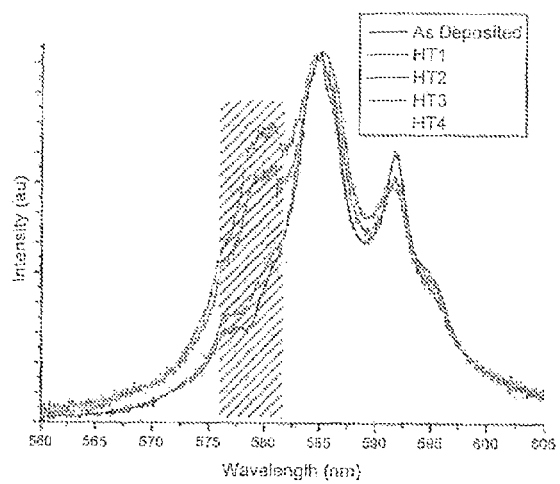
Figure 3B:
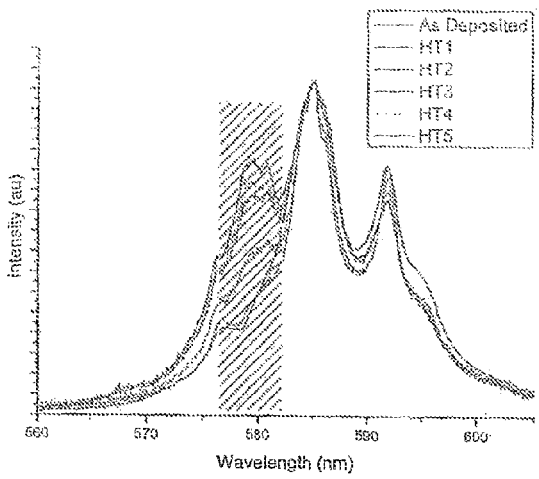
Figure 3C:
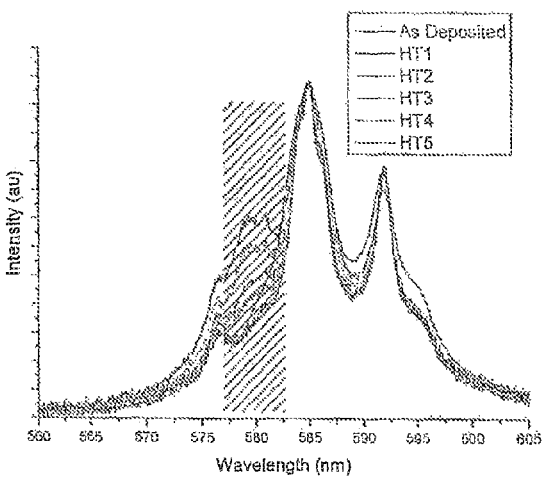
Figure 4A:
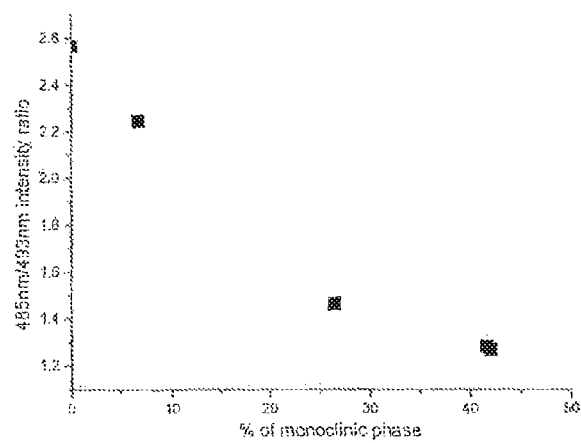
Figure 4B:
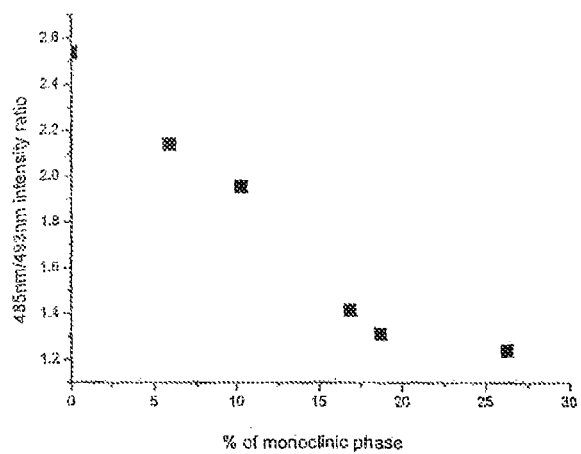
Figure 4C:
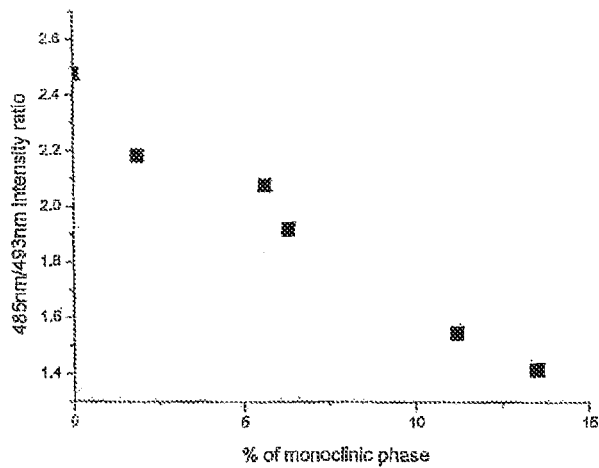
Figure 5A:
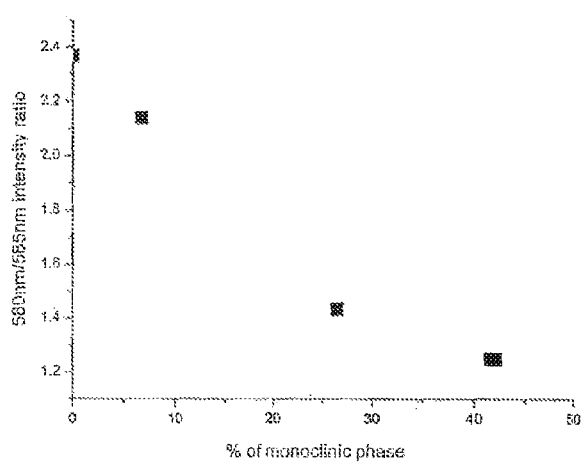
Figure 5B:
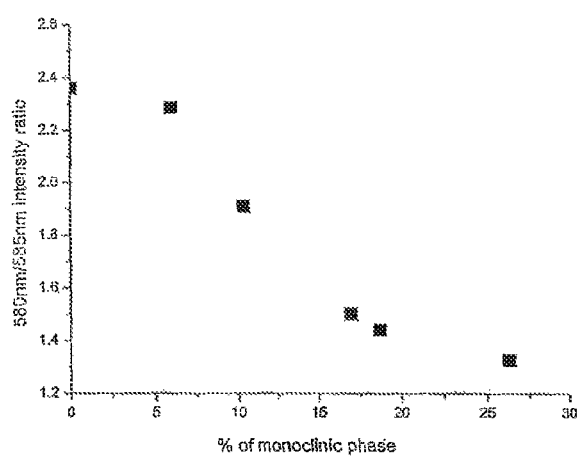
Figure 5C:
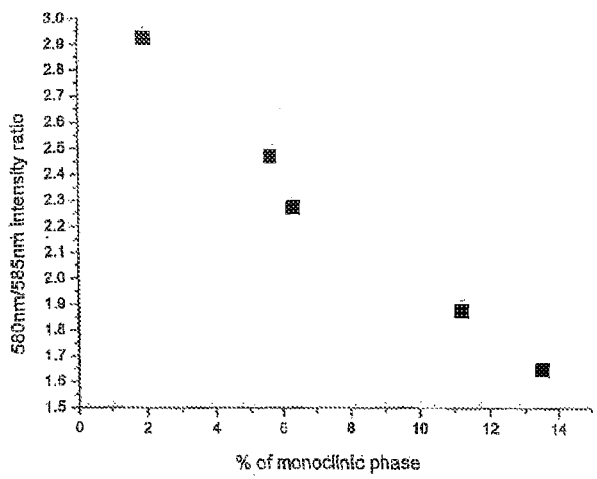
Figure 6:
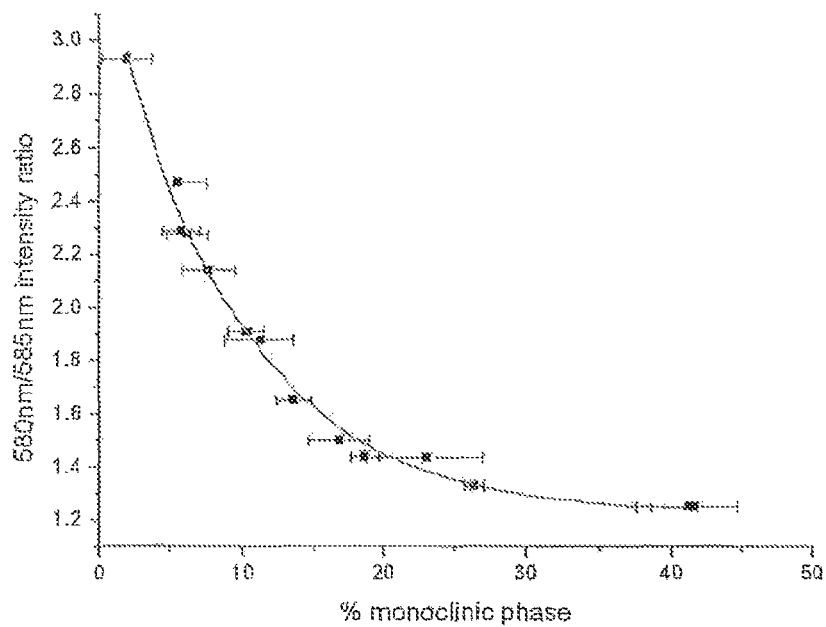
Figure 7:
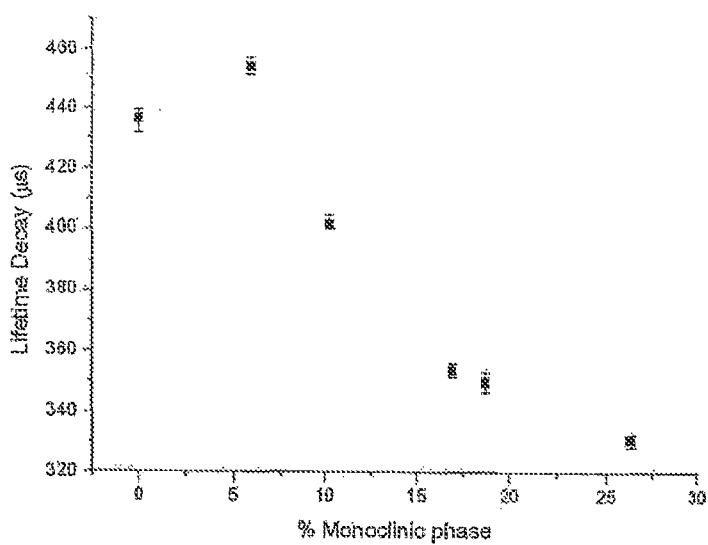
Figure 8A:
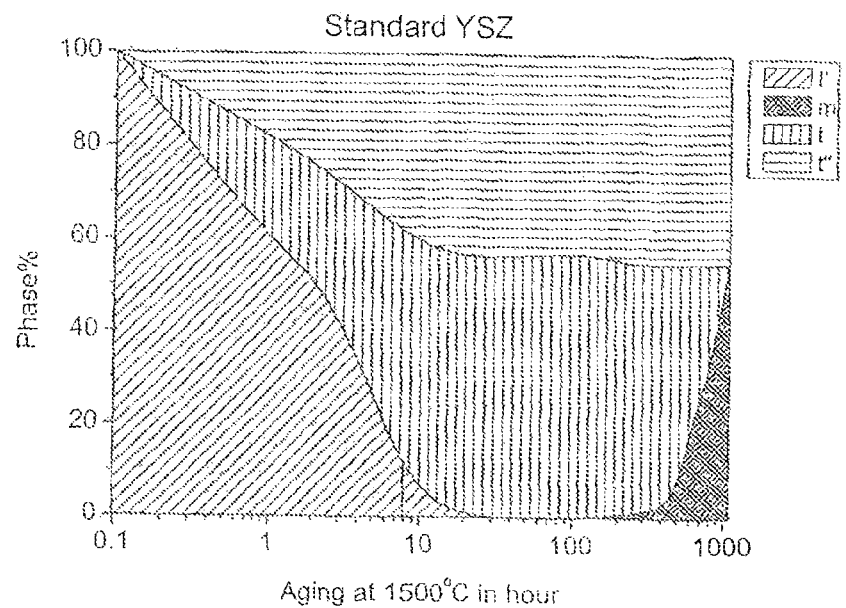
Figure 8B:
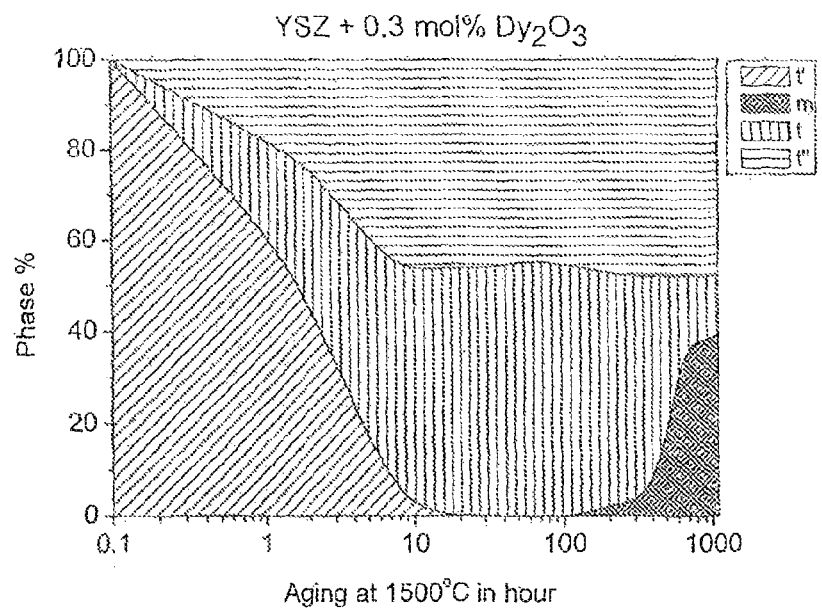
Figure 8C:
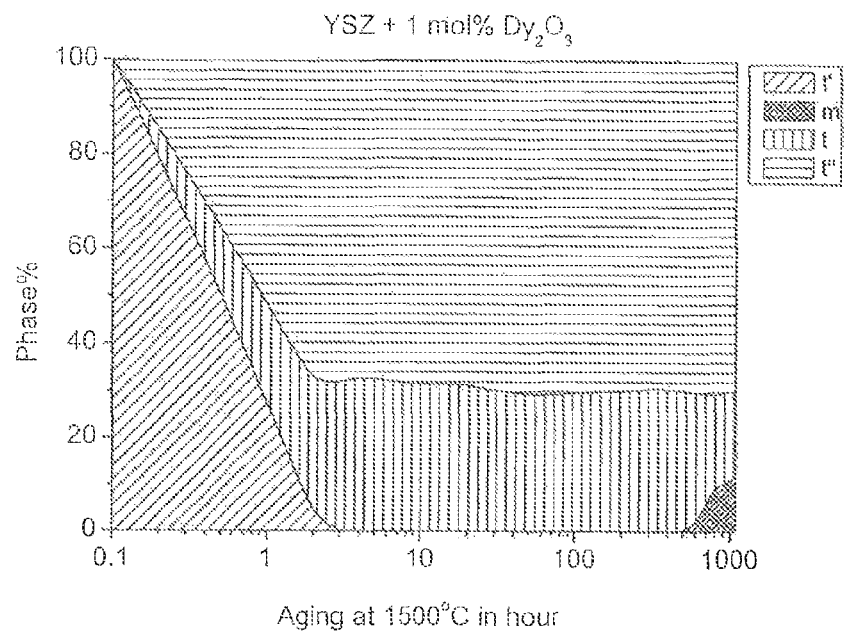
Figure 8D:
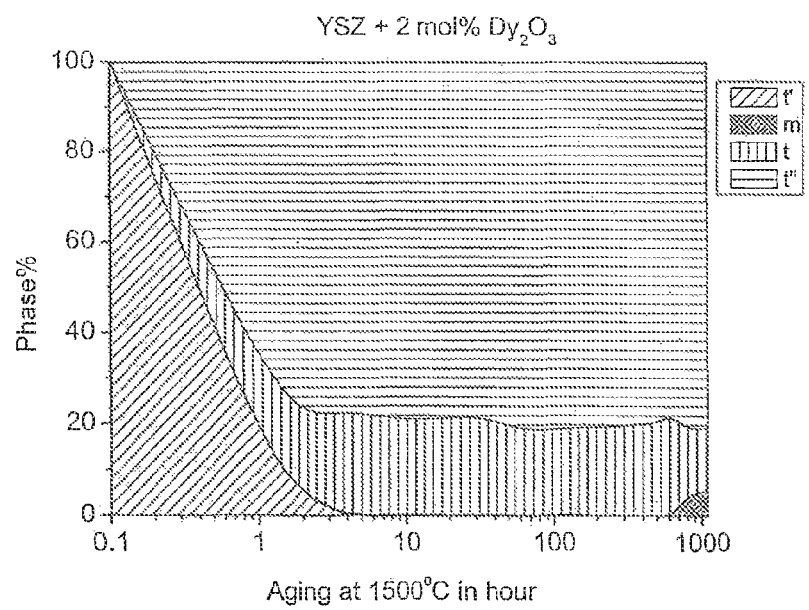
Figure 9:
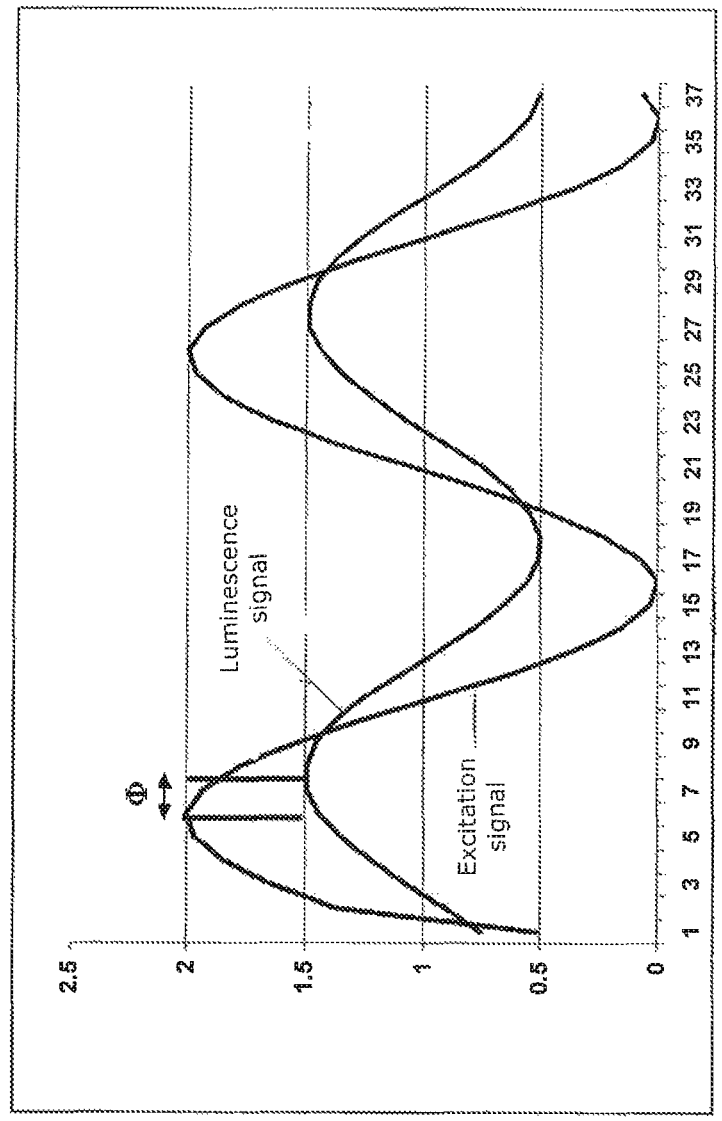

Preferred embodiments of the present invention will now be described hereinbelow by way of example only with reference to the accompanying drawings, in which:

FIG. 1 illustrates a TBC as applied to an object in accordance with one embodiment of the present invention;

FIGS. 2(a) to (c) illustrate normalized phosphorescence spectra for samples comprising 7 wt % YSZ+0.3 mol % $Dy_2O_3$, 7 wt % YSZ+1 mol % $Dy_2O_3$ and 7 wt % YSZ+2 mol % $Dy_2O_3$;

FIGS. 3(a) to (c) illustrate normalized phosphorescence spectra for samples comprising 7 wt % YSZ+0.3 mol % $Dy_2O_3$, 7 wt % YSZ+1 mol % $Dy_2O_3$ and 7 wt % YSZ+2 mol % $Dy_2O_3$;

FIGS. 4(a) to (c) illustrate intensity ratios of the peaks at about 485 nm and about 493 nm as a function of the percentage of the m phase for samples comprising 7 wt % YSZ+0.3 mol % $Dy_2O_3$, 7 wt % YSZ+1 mol % $Dy_2O_3$ and 7 wt % YSZ+2 mol % $Dy_2O_3$;

FIGS. 5(a) to (c) illustrate intensity ratios of the peaks at about 580 nm and about 585 nm as a function of the percentage of the m phase for samples comprising 7 wt % YSZ+0.3 mol % $Dy_2O_3$, 7 wt % YSZ+1 mol % $Dy_2O_3$ and 7 wt % YSZ+2 mol % $Dy_2O_3$;

FIG. 6 illustrates the intensity ratios for the peaks at about 580 nm and about 585 nm as a function of the percentage of the m phase for the three different dopant concentrations 7 wt % YSZ+0.3 mol % $Dy_2O_3$, 7 wt % YSZ+1 mol % $Dy_2O_3$ and 7 wt % YSZ+2 mol % $Dy_2O_3$;

FIG. 7 illustrates the luminescence life-time decay at room temperature as a function of the percentage of the m phase for the series of samples comprising 7 wt % YSZ+1 mol % $Dy_2O_3$;

FIGS. 8(a) to (d) represent the phase compositions for samples comprising 7 wt % YSZ, 7 wt % YSZ+0.3 mol % $Dy_2O_3$, 7 wt % YSZ+1 mol % $Dy_2O_3$ and 7 wt % YSZ+2 mol % $Dy_2O_3$ where aged at a temperature of 1500° C.; and FIG. 9 illustrates excitation and luminescence signals for an aged sample where obtained by a method of detecting ageing in accordance with a preferred embodiment of the present invention.

FIG. 1 illustrates a coating 1, in this embodiment a TBC, as applied to an object 3 in accordance with one embodiment of the present invention.

In one embodiment the present invention relates to a luminescent material composition, and structures incorporating the same, such as TBCs, which comprises a zirconia host containing at least one luminescent lanthanide oxide additive, in particular a tri-valent lanthanide oxide additive ($L_2O_3$, where L is a lanthanide), and in particular dysprosia ($Dy_2O_3$). As will be described in more detail hereinbelow, dysprosia is effective in stabilizing zirconia in a thermal environment, such as both to delay the onset and reduce the extent of the detrimental formation of the m phase, and also provides for luminescent temperature sensing, thereby advantageously conferring multi-functionality.

In a preferred embodiment the present invention relates to a luminescent material composition, and structures incorporating the same, such as TBCs, which comprises yttria ($Y_2O_3$) partially-stabilized zirconia containing a tertiary addition of a luminescent lanthanide oxide, in particular a tri-valent lanthanide oxide additive, such as dysprosia ($Dy_2O_3$). The tertiary addition of a lanthanide oxide to yttria partially-stabilized zirconia further improves the phase stability and also provides for luminescent temperature sensing, thereby again conferring multi-functionality.

In other embodiments the lanthanide oxide additive can comprise any of ceria ($CeO_2$), praseodymia ($Pr_6O_{11}$), neodymia ($Nd_2O_3$), promethia ($Pm_2O_3$), samaria ($Sm_2O_3$), europia ($Eu_2O_3$), gadolinia ($Gd_2O_3$), terbia ($Tb_4O_7$), holmia ($Ho_2O_3$), erbia ($Er_2O_3$), thulia ($Tm_2O_3$) and ytterbia ($Yb_2O_3$).

In a preferred embodiment the lanthanide oxide addition is between about 0.003 and about 4 mol %, preferably between about 0.01 and about 4 mol %, and more preferably between about 0.3 and about 2 mol %.

In exemplary embodiments samples comprising 7 wt % YSZ co-doped with 0.3, 1 and 2 mol % of $Dy_2O_3$, respectively, were deposited as coatings, here TBCs, by EB-PVD.

The samples were subsequently subjected to heat treatments (HT) of from 0.1 to 1000 hours at 1500° C. to produce coatings with different amounts of the m phase. For each heat treatment, the phase composition of the coatings was determined by XRD.

FIGS. 2(a) to (c) and 3(a) to (c) illustrate normalized phosphorescence spectra for the samples comprising 7 wt % YSZ+0.3 mol % $Dy_2O_3$, 7 wt % YSZ+1 mol % $Dy_2O_3$ and 7 wt % YSZ+2 mol % $Dy_2O_3$. As will be observed, the emission spectra of the heat treated samples have characteristic peaks at wavelengths of about 493 nm and about 580 nm, and the intensity of these peaks increases with increasing ageing time. The peak at about 493 nm is also shifted towards lower wavelengths with ageing.

FIGS. 4(a) to (c) illustrate the intensity ratios of the peak at about 485 nm and the growing peak at about 493 nm as a function of the percentage of the m phase for the samples comprising 7 wt % YSZ+0.3 mol % $Dy_2O_3$, 7 wt % YSZ+1 mol % $Dy_2O_3$ and 7 wt % YSZ+2 mol % $Dy_2O_3$.

FIGS. 5(a) to (c) illustrate the intensity ratios of the peak at about 580 nm and the growing peak at about 585 nm as a function of the percentage of the m phase for the samples comprising 7 wt % YSZ+0.3 mol % $Dy_2O_3$, 7 wt % YSZ+1 mol % $Dy_2O_3$ and 7 wt % YSZ+2 mol % $Dy_2O_3$.

As can observed, the intensity ratios follow the same trend, with the intensity ratio decreasing exponentially as the proportion of the m phase increases. For higher percentages of the m phase, the intensity ratio tends towards a minimum value of about 1.2.

FIG. 6 illustrates the intensity ratios for the peaks at about 580 nm and about 585 nm as a function of the percentage of the m phase for the three different dopant concentrations 7 wt % YSZ+0.3 mol % $Dy_2O_3$, 7 wt % YSZ+1 mol % $Dy_2O_3$ and 7 wt % YSZ+2 mol % $Dy_2O_3$. This plot shows surprisingly good agreement for the different dopant concentrations, indicating that a determination of the proportion of the m phase can be made using the peak ratios for these emission lines, and also that this is independent of the dopant concentration.

The data was fitted with an exponential function having the following equation:

$$R = a \cdot \exp(-\%m/b) + c$$

Where: a, b and c are constants which can be pre-calibrated, R is the intensity ratio and % m is the percentage of the m phase.

For the concentrations of dysprosia as employed in the preferred embodiments, the constants are a=2.15, b=9.98 and c=1.22, though the constants could be taken within the range of a=2 to 2.3, b=9 to 11 and c=1 to 1.4.

The exponential characteristic of the intensity ratio is particularly advantageous, in enabling much better accuracy in the detection of the proportion of the m phase and thus enabling much better life-time prediction.

The exponential characteristic is also particularly surprising in that U.S. Pat. No. 6,730,918, which studied a YSZ:Eu phosphor, discloses a linear relationship between intensity ratio and the proportion of the m phase.

The present invention also provides for phase detection based on the life-time decay of the phosphorescence.

As is well known, after illumination with a pulsed excitation light source, the phosphorescence starts to decay, and the life-time decay of the phosphorescence usually follows a single or multi-exponential decay, where a decay constant tau is determined by a fitting routine. Furthermore, the luminescence life-time decay at room temperature is affected by the crystallographic structure of the phosphor.

FIG. 7 illustrates the luminescence life-time decay at room temperature as a function of the percentage of the m phase for the series of samples comprising 7 wt % YSZ+1 mol % $Dy_2O_3$.

It is postulated that the luminescence life-time decay at room temperature increases when the t' phase separates into the t and c phases and then decreases exponentially as the proportion of the m phase increases, and, on this basis, the life-time decay is used in the present invention to monitor the destabilization of structures, such as TBCs.

This method enables the calculation of an 'integrated-time-at-temperature' against the m phase transformation.

This behaviour is illustrated in FIGS. 8(a) to (d) for a temperature of 1500° C., which represent the phase compositions for samples comprising 7 wt % YSZ, 7 wt % YSZ+0.3 mol % Dy$_2$O$_3$, 7 wt % YSZ+1 mol % Dy$_2$O$_3$ and 7 wt % YSZ+2 mol % Dy$_2$O$_3$, where the proportion of the m phase increases with the exposure time at times above about 100 h. At different temperatures, the time to the onset of m phase formation will change, occurring earlier at higher temperatures. Thus, in conjunction with surface temperature measurement, these plots allow the remaining useful life-time to be determined from a phase stability perspective.

In a further embodiment the present invention provides a method of detecting ageing of materials by reference to phase differences between an excitation source and the luminescence in periodically excited sensor materials.

The excitation source can be any variable excitation source and does not need to be a pulsed laser. Other alternative excitation sources are LEDs, mercury vapour lamps and other gas lamps having the appropriate excitation wavelength.

When the excitation source changes its output periodically, but continuously, the response of the phosphor will follow this periodic signal with a delay. The length of the delay is dependent upon the ability of the phosphor to follow the excitation signal and this is determined by the material phase composition, which affects the luminescence life-time decay or response time. A very fast response would show no delay and the excitation signal and the luminescence would occur at almost the same time. If the response of the luminescence material is slower, the phosphorescence would also be delayed and there would be a difference between the phase of the excitation signal and the phosphorescence signal. This principle is applicable where the life-time decay of a particular material is insensitive to temperature or pressure changes, or where these changes are calibrated and known.

EXAMPLE

Using an illumination source, here an LED or a mercury lamp, where the intensity varies periodically with a sinusoidal wave function, the luminescence signal is phase shifted as illustrated in FIG. 9. The phase shift can easily be established by determining the temporal position of the peak positions of the stimulating light source and the phosphorescence response.

The ageing can be determined by comparing the results with a predetermined phase shift-to-ageing calibration table.

The main advantage of this technique is the absence of the detection of intensities, which will enable the method to work more precisely than any other intensity-related method.

The phase difference which occurs due to a change in the luminescence life-time decay enables a high degree of detection accuracy, which is not limited by intensity variations, which could occur due to the presence of dirt or other pollution on the detection optics. It also enables repeated accumulated measurements which gives another distinct advantage. Once a phase difference between the external light source and the luminescence signal has been measured and a relation between the phase difference and the ageing has been calibrated, the method can be used to detect the ageing by detecting the phase change difference.

The doped material which is aged has the following luminescence output I:

$$I = 1 + m \cdot \sin(2\pi f t - \Phi)$$

m: modulation depth
π: Pi
f: frequency of the excitation source
t: time
Φ: phase difference $$\tan(\Phi) = 2\pi f \tau$$

τ: life-time decay

Finally, it will be understood that the present invention has been described in its preferred embodiments and can be modified in many different ways without departing from the scope of the invention as defined by the appended claims.

The invention claimed is:

1. A method of determining the proportion of a monoclinic phase (m) in a luminescent material composition comprising a zirconia host and containing a luminescent lanthanide oxide additive, the method comprising the steps of:
   determining an intensity ratio for a pair of luminescent emission lines for the material composition which decreases exponentially as a function of the proportion of the m phase in the material composition;
   fitting the intensity ratio to an exponential function for the material composition; and
   determining the proportion of them phase in the material composition.

2. The method of claim 1, wherein the lanthanide oxide additive is a tri-valent lanthanide oxide.

3. The method of claim 1, wherein the lanthanide oxide additive is included in an amount of between about 0.003 and about 4 mol %.

4. The method of claim 1, wherein the material composition further contains yttria (Y$_2$O$_3$) and the zirconia is partially stabilized by the yttria.

5. The method of claim 1, wherein the exponential function is fitted by the equation R=(a·exp(−% m/b))+c, where a, b and c are pre-calibrated constants, R is the intensity ratio and % m is the percentage of the m phase.

6. The method of claim 1, wherein the exponential function is substantially independent of the amount of the lanthanide oxide additive.

7. The method of claim 1, wherein the emission lines are at wavelengths of about 485 nm and about 493 nm or about 580 nm and about 585 nm.

8. The method of claim 1, wherein the method is for determining a remaining useful life-time for the material composition, and the method further comprises the step of:
   determining a remaining useful life-time for the material composition by reference to the proportion of them phase in the material composition.

9. The method of claim 1, wherein the lanthanide oxide additive is dysprosia (Dy$_2$O$_3$).

10. The method of claim 1, wherein the lanthanide oxide additive is included in an amount of between about 0.01 and about 4 mol %.

11. The method of claim 1, wherein the lanthanide oxide additive is included in an amount of between about 0.3 and about 2 mol %.

12. A method of determining the proportion of a monoclinic phase (m) in a luminescent material composition comprising a zirconia host and containing a luminescent lanthanide oxide additive, the method comprising the steps of:
   determining a luminescence life-time decay at room temperature for the material composition;

fitting the determined life-time decay to a life-time decay curve calibrated as a function of the proportion of the m phase for the material composition; and determining the proportion of the m phase in the material composition.

13. The method of claim 12, wherein the lanthanide oxide additive is a tri-valent lanthanide oxide.

14. The method of claim 12, wherein the lanthanide oxide additive is included in an amount of between about 0.003 and about 4 mol %.

15. The method of claim 12, wherein the material composition further contains yttria ($Y_2O_3$) and the zirconia is partially stabilized by the yttria.

16. The method of claim 12, wherein the method is for determining a remaining useful life-time for the material composition, and the method further comprises the step of:

determining a remaining useful life-time for the material composition by reference to the proportion of the m phase in the material composition.

17. The method of claim 12, wherein the lanthanide oxide additive is dysprosia ($Dy_2O_3$).

18. The method of claim 12, wherein the lanthanide oxide additive is included in an amount of between about 0.01 and about 4 mol %.

19. The method of claim 12, wherein the lanthanide oxide additive is included in an amount of between about 0.3 and about 2 mol %.

20. A method of determining ageing of a material, the method comprising the steps of:

applying an excitation signal having a periodically-varying intensity to a material including a luminescent element;

detecting a luminescence signal from the material;

determining a phase relationship between the excitation and luminescence signals; and determining ageing of the material from the phase relationship between the excitation and luminescence signals.

21. The method of claim 20, wherein the excitation signal has a sinusoidal waveform.

22. The method of claim 20, wherein the phase relationship between the excitation and luminescence signals is referenced to a look-up table.

23. The method of claim 20, wherein the ageing of the material relates to a structural phase change.

24. The method of claim 20, wherein the material comprises a zirconia host containing a luminescent lanthanide oxide additive.

25. The method of claim 24, wherein the ageing of the material relates to the proportion of a monoclinic (m) phase in the material.

26. A method for determining a remaining useful life-time of a luminescent material composition comprising a zirconia host containing a luminescent lanthanide oxide additive, the method comprising the steps of:

applying an excitation signal having a periodically-varying intensity to the material composition;

detecting a luminescence signal from the material composition;

determining a phase relationship between the excitation and luminescence signals;

determining the proportion of a monoclinic (m) phase in the material composition; and determining a remaining useful life-time for the material composition by reference to the proportion of the m phase in the material.

* * * * *